(12) United States Patent
Lange

(10) Patent No.: US 6,180,943 B1
(45) Date of Patent: Jan. 30, 2001

(54) TOMOGRAPH ACQUISITION APPARATUS HAVING A PAIR OF ROTATABLE SCINTILLATION DETECTORS WHICH FORM DETECTION FIELDS AT AN ANGLE OF INCLINATION RELATIVE TO EACH OTHER

(75) Inventor: Kai Lange, Vedbaik (DK)

(73) Assignee: General Electric Company, Milwaukee, WI (US)

( * ) Notice: Under 35 U.S.C. 154(b), the term of this patent shall be extended for 0 days.

(21) Appl. No.: 08/150,020

(22) PCT Filed: Oct. 23, 1991

(86) PCT No.: PCT/EP91/02045

§ 371 Date: Nov. 8, 1993

§ 102(e) Date: Nov. 8, 1993

(87) PCT Pub. No.: WO92/07512

PCT Pub. Date: May 14, 1992

(30) Foreign Application Priority Data

Oct. 26, 1990 (DK) .................................................. 2577/90

(51) Int. Cl.[7] .................................................. G01T 1/166
(52) U.S. Cl. ................................. 250/363.05; 250/363.04
(58) Field of Search ........................... 250/363.04, 363.05

(56) References Cited

U.S. PATENT DOCUMENTS

| 4,368,389 | 1/1983 | Blum ........................................ 378/20 |
| 4,417,143 | 11/1983 | Haas . |
| 4,590,378 | 5/1986 | Platz ...................................... 378/198 |

FOREIGN PATENT DOCUMENTS

| 0092437 | 10/1983 | (EP) . |
| 2250670 | * 6/1992 | (GB) ............................. 250/363.04 |

* cited by examiner

Primary Examiner—Constantine Hannaher
(74) Attorney, Agent, or Firm—James O. Skarsten; Christian G. Cabou; Phyllis Y. Price

(57) ABSTRACT

To acquire tomographs, two detectors (1, 2) are secured together in a support structure (3) in such a manner that their detection fields are inclined relative to each other. The angle of inclination between them is preferably 90°. This pair of detectors is then placed in such a manner that the plane (9) bisecting the two detection fields includes the axis of rotation (4) around which the pair of detectors is to rotate to perform tomography on a subject. For fat subjects, the pair is moved away (13) from the axis, and for thin subjects it is moved towards it. It is shown that to avoid detector displacement interfering with tomography computation, it suffices merely to change computation parameters in the reconstruction algorithm.

13 Claims, 5 Drawing Sheets

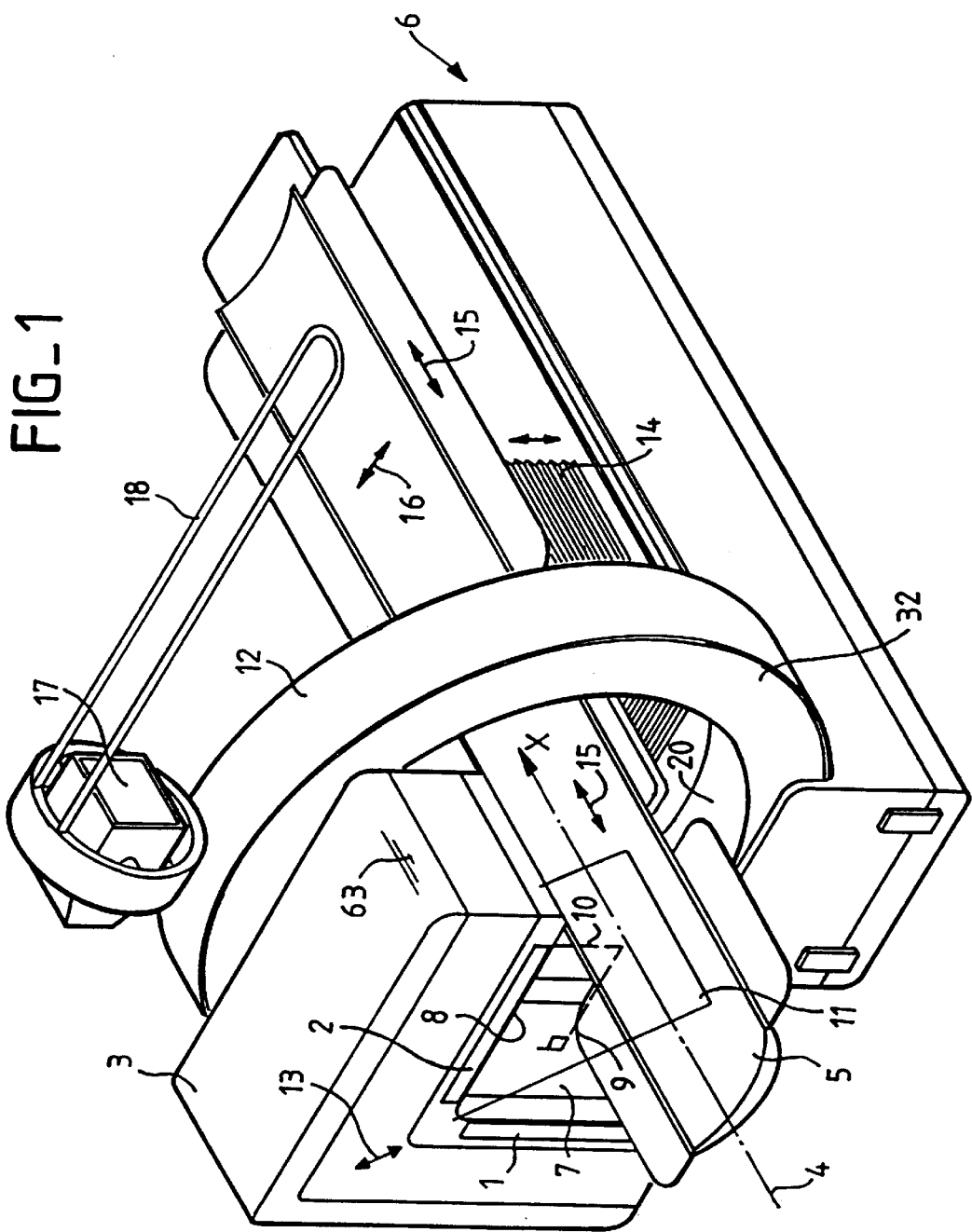
FIG_1

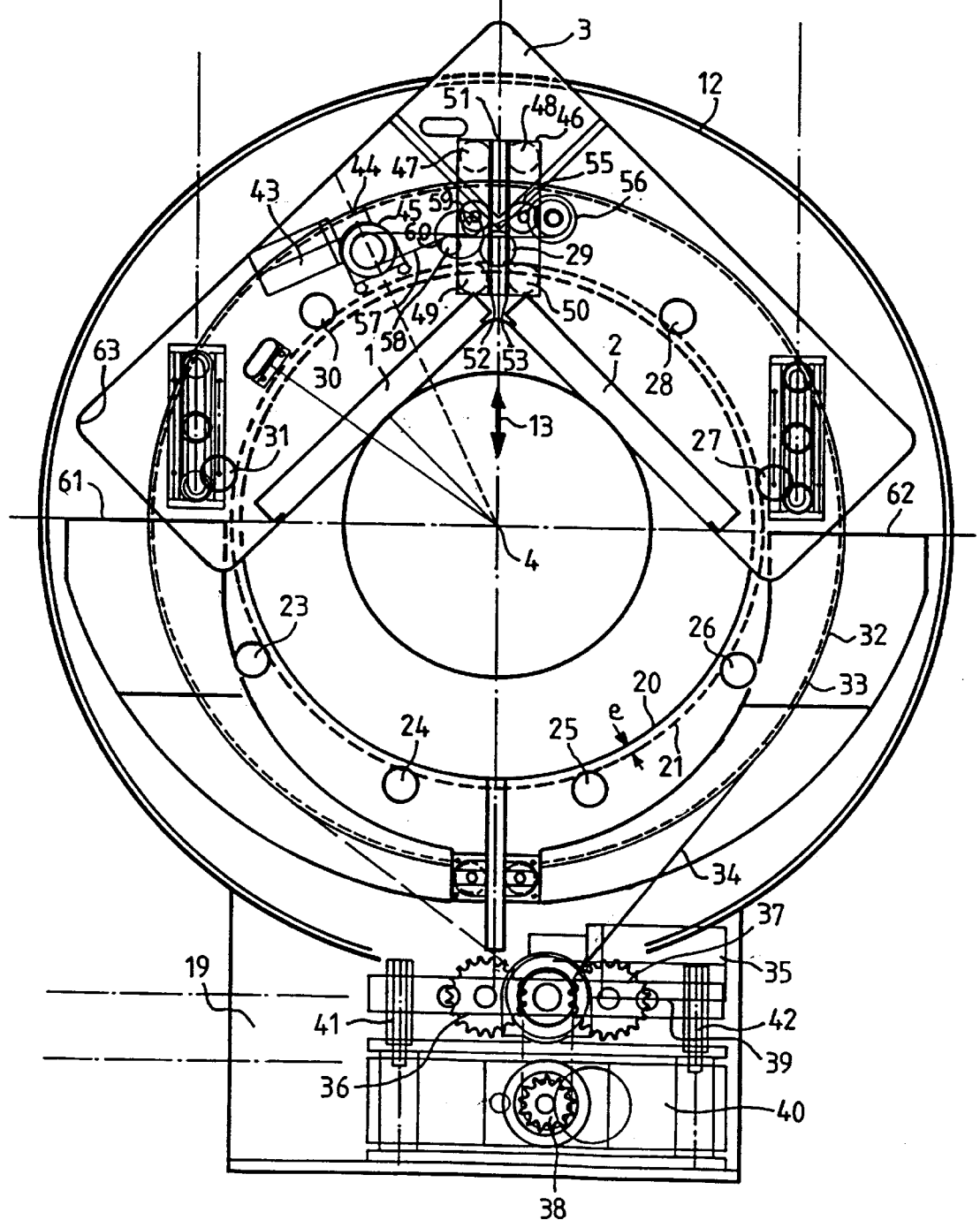
FIG_2

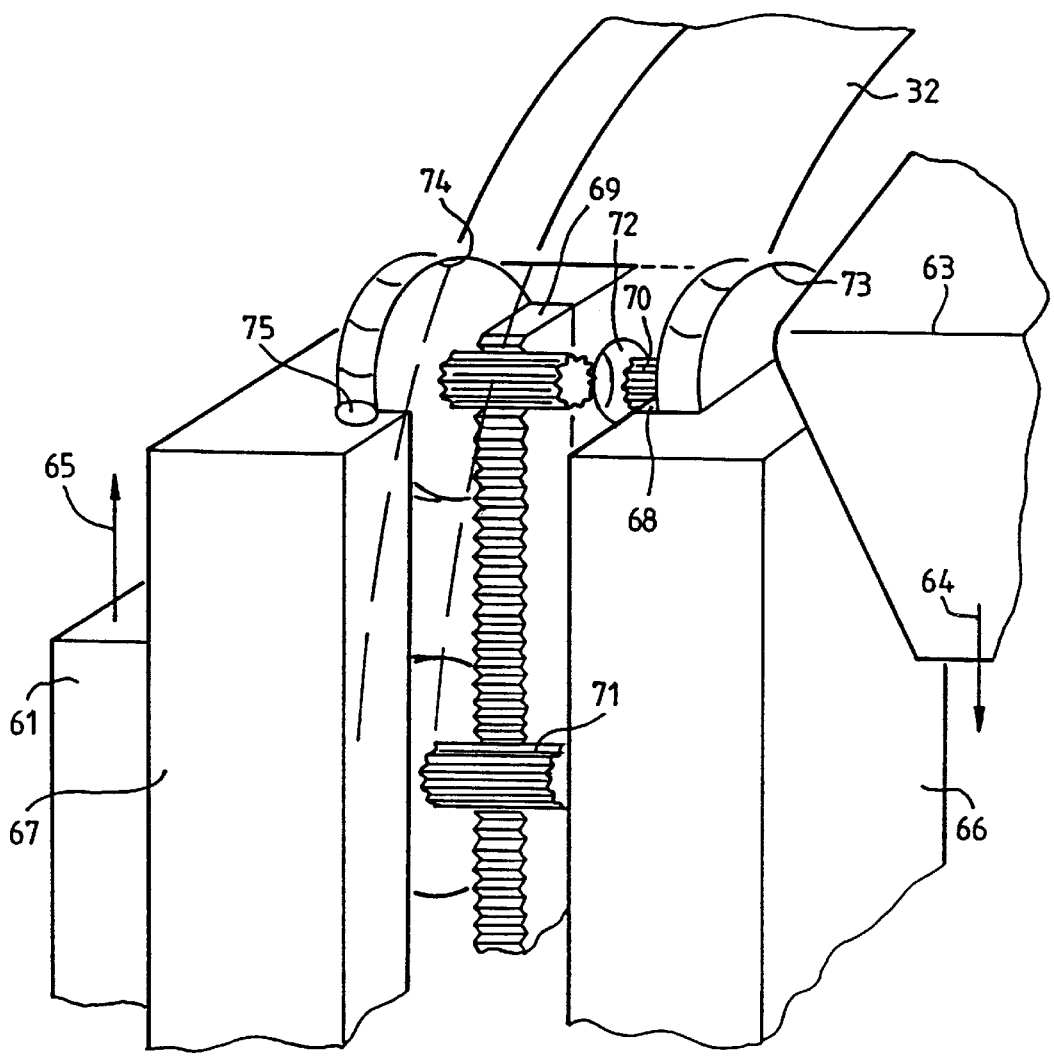
FIG_3

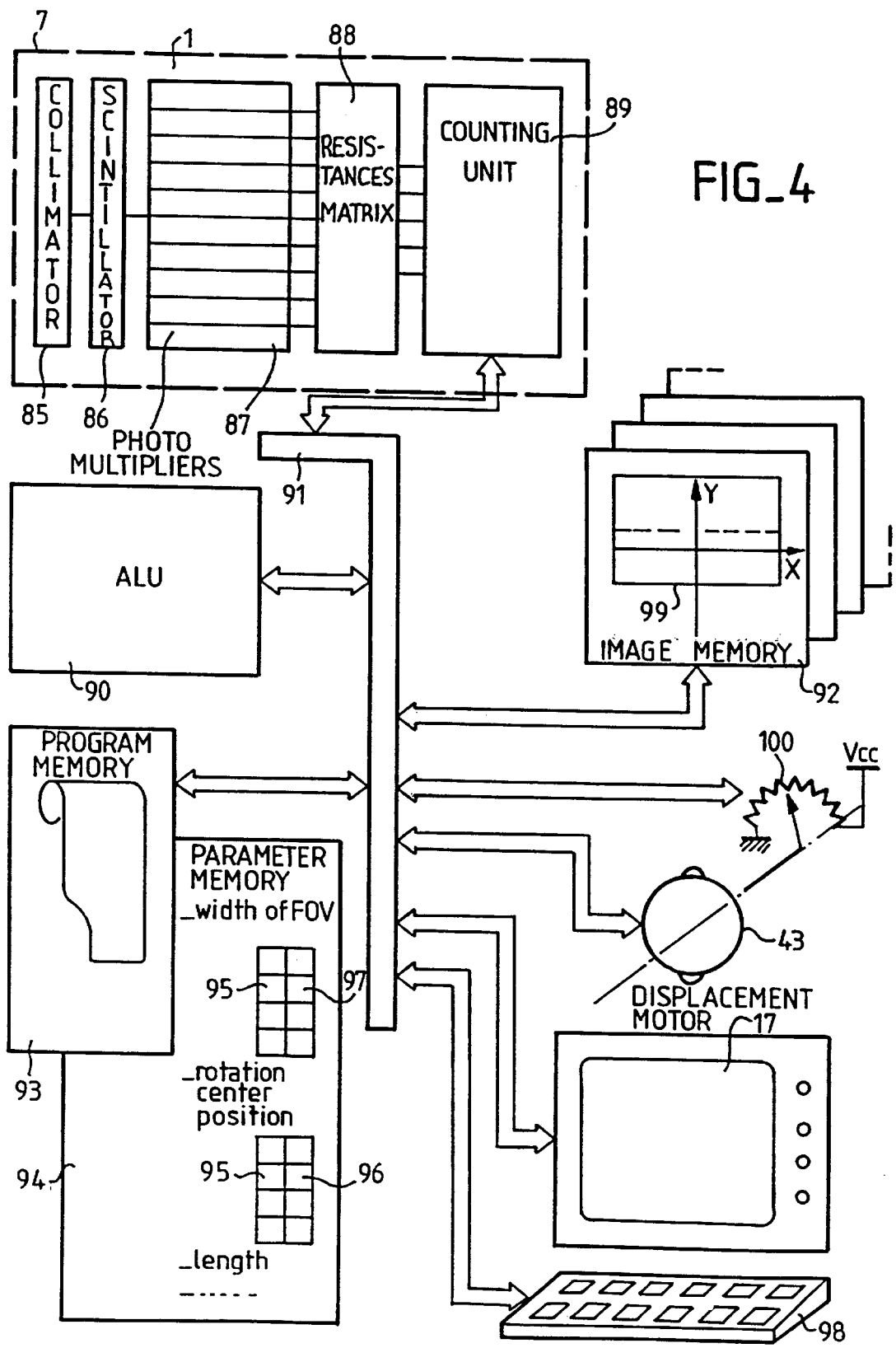

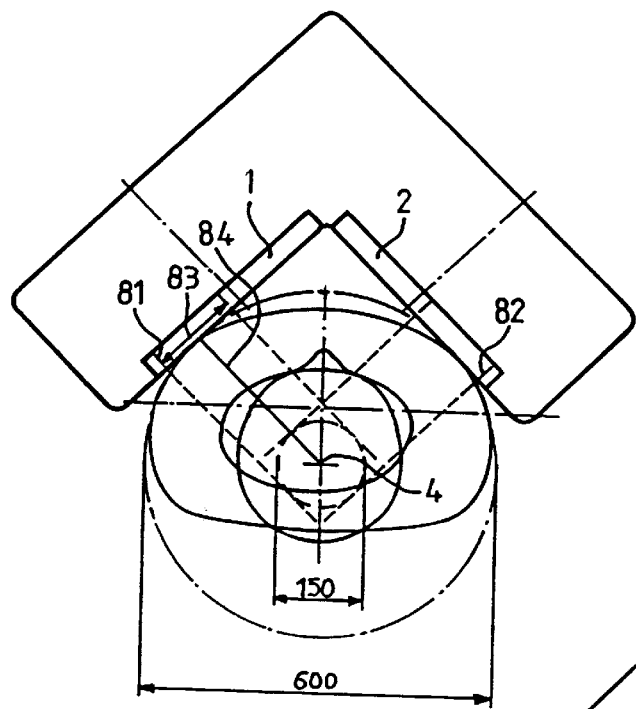
FIG_5a
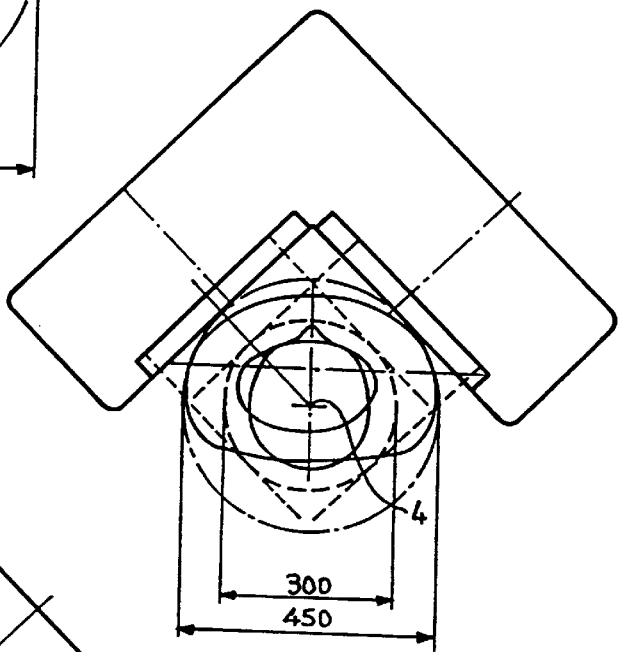
FIG_5b
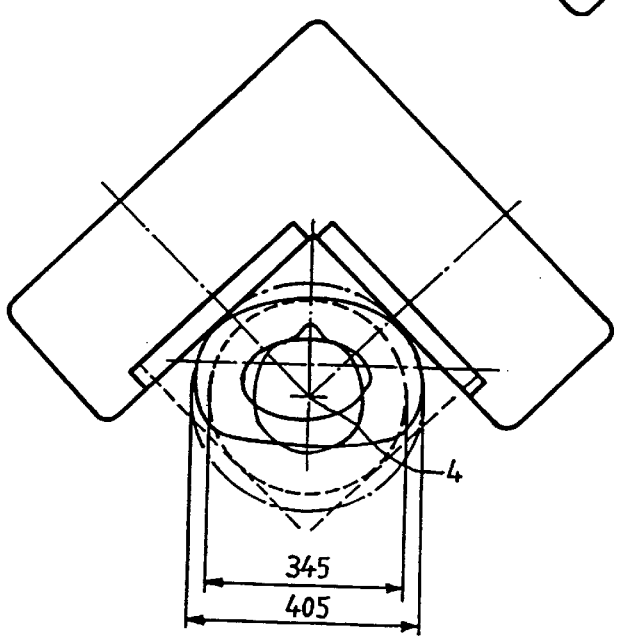
FIG_5c

TOMOGRAPH ACQUISITION APPARATUS HAVING A PAIR OF ROTATABLE SCINTILLATION DETECTORS WHICH FORM DETECTION FIELDS AT AN ANGLE OF INCLINATION RELATIVE TO EACH OTHER

BACKGROUND OF THE INVENTION

The present invention relates to tomograph acquisition apparatus usable, in particular, in the medical field. It relates essentially to acquiring tomographs with scintigraphy detectors that are easy to use.

The principles of scintigraphy detectors is known in nuclear medicine. They are as follows. A radioactive marker, generally technetium, is injected into a patient. As a function of its nature, the marker is distributed from its point of injection into various portions of the patient's body. In the patient's body, the marker is to be found in the organ under investigation and it reveals the function thereof. The marker produces gamma photons. After passing through a collimator, the gamma photons are detected by a scintillator crystal, whence the term "scintigraphy detector". The crystal transforms the gamma photons into light photons. The light photons are in turn detected by photomultiplier tubes placed looking at the scintillator. The currents that flow through the photomultiplier tubes are in the form of pulses and are a function of the magnitude of the scintillation produced. These currents are applied to a resistance matrix. The resistance matrix outputs "locating" pulses that specify the position at which scintillation took place facing the photomultiplier tubes.

A counter unit connected to the output from the resistance matrix serves to sum the number of such pulses occurring at each location on the scintillator. It is then possible to create an image representative of the activity of the marker in the body by attributing brightness to each image point as a function of the number of strikes that have been counted for each of said locations. Such a method is known in the state of the art under the name "Anger" method. With very fast scintigraphy cameras, e.g. capable of counting up to 200,000 strikes per second, an image constituting a projection of a portion of the human body can be generated in about 30 seconds.

The detector is mounted in a rotary assembly called a gamma camera which also serves to aim the detector. If the detector is aimed in different directions relative to the body, multiple images can be acquired under the same conditions. By acquiring a sufficient number of images for different aiming directions of the detector, the set of image signals can be subjected to processing suitable for obtaining tomographs of the body by algorithmic reconstruction. Given that the accuracy of such tomographic images increases with the number of projection images, it can be seen that such a method leads to periods of examination that are relatively long.

Proposals have already been made to remedy this problem by constructing gamma cameras provided with two, three, or even more detectors. Under such circumstances, the duration of an examination is reduced, substantially pro rata the number of detectors.

However, another problem arises. To obtain projection images, and consequently tomographs, that have very good resolution, it is necessary for the detectors to be placed as close as possible to the body. Unfortunately, patients to be examined are not all the same size, some are fat, others are thin. In addition, depending on the examination being performed, it may be necessary for the detectors to be at various different distances from the body. For example, an examination around the belly requires the detectors to be at a different distance from the patient than an examination around the head, since the diameter of the head is smaller. A known way of solving this problem is to mount the detectors on telescopic arms and to move the detectors initially as close as possible to the patient. During an examination, the detector travels around a circle whose diameter depends on said distance from the patient. A device of this kind is for example depicted in U.S. Pat. No. 4,368,389.

The drawback of such a telescopic mechanism is that it is twice as complex when there are two detectors instead of only one, and so on. The telescopic mechanism is itself mounted on a rotary assembly enabling the detectors to be pointed in different image-taking directions.

SUMMARY OF THE INVENTION

An object of the invention is to remedy these drawbacks firstly by taking account of the need to place more than one detector on the rotary assembly in order to accelerate acquisition, and secondly to simplify the handling of the various detectors. To solve these problems, the invention begins by securing the two detectors to each other and also by giving them a certain angle of inclination relative to each other.

Thus, any one detector has a substantially plane detection surface constituting its detection field. At present, such detection fields are rectangular in shape. They have a length and they have a width. In the invention, two detectors are placed against each other so that the normals to the centres of their detection fields intersect, and so that these detection fields are adjacent to each other along one side of each of them, which sides are called "lengths". In the following explanation, the adjacent sides are called lengths, but that does not mean that the detection field is necessarily longer in that direction than it is along a direction at rightangles.

It is preferable for the normals to intersect at an angle of 90°. However, this is not essential and the angle could be acute or obtuse. The two detectors are thus secured to each other in this configuration in such a manner that the bisector plane including the point of intersection of the normals and the adjacent lengths of the two detectors also contains the axis of rotation of the tomography.

With small patients, the assembly is displaced radially towards the axis of rotation. The corner formed by the two detectors can thus be moved closer to a small patient on the axis of the machine. Alternatively the corner can be moved further away when examining a fat patient, likewise on the axis of the machine. This simplifies the displacement mechanics.

However, by acting in this way, the information acquired during projection is not properly situated since the axis of rotation of the machine does not necessarily pass through the point of intersection of the normals to the detection fields. To be able to use the same reconstruction algorithms, it is therefore necessary to transform the image signal processing parameters as a function of the distance between the pair of detectors and the axis of rotation. It is shown that exactly the same algorithms can be used to reconstitute tomography images, while also obtaining a substantial saving on the mechanical equipment which is much simpler.

The invention thus provides an apparatus for acquiring tomographs of a subject, the apparatus comprising a pair of plane scintillation detectors carried by a support rotating about an axis of rotation, and connected to an image processor, the apparatus being characterised in that:

the detection fields of these two detectors are inclined at an angle relative to each other;

the bisector plane bisecting the angle formed between these detection fields includes the axis of rotation;

and in that the apparatus includes:

means for displacing the pair of detectors together relative to the subject in a direction which is radial to the axis of rotation; and modification means for modifying an effective detection field of these detectors as a function of said displacement.

The invention will be better understood on reading the following description and examining the accompanying drawings. The drawings are given merely by way of indication and do not limit the invention in any way. In the drawings:

BRIEF DESCRIPTION OF THE DRAWINGS

FIG. 1 is a perspective view of acquisition apparatus of the invention;

FIG. 2 is a section through the mechanism for rotating the detectors and moving them relative to the axis of rotation;

FIG. 3 is a perspective diagram of a mechanical detail enabling the detectors and their counterweights to be moved simultaneously;

FIG. 4 is a block diagram of the set of means implemented by the invention; and

FIGS. 5a to 5c are diagrams of the diameters that can be fully reconstructed for three different sizes of patient.

DETAILED DESCRIPTION OF THE PREFERRED EMBODIMENT

FIG. 1 shows tomography acquisition apparatus of the invention. It includes a pair of plane detectors 1 and 2 carried together by a common support 3. The support 3 rotates about an axis of rotation 4. The axis of rotation lies slightly above the top surface 5 of the bed 6 that carries a patient being examined by the machine. By acting in this way, the axis 4 is caused to lie substantially in the middle of the patient. Both of the detectors 1 and 2 are connected to an image processing apparatus that is explained below. The detection fields 7 and 8 of the detectors 1 and 2 respectively are at an angle relative to each other. Their adjacent edges, named length, are spaced apart from each other, in one example with a 2 cm space, but preferably this space is less that 8 or 10 cm.

In the example shown they are inclined at an angle of substantially 90° to each other and their respective centre-of-field normals 9 and 10 intersect at a right angle. A bisector plane 11 contains the bisector of the angle formed by the detection fields 7 and 8 and also contains the axis of rotation 4. The set of two detectors 1 and 2 is rotatable about the axis of rotation 4 by rotating a ring 32 carried by a circular cover 12. According to an essential characteristic of the invention, the set 3 of detectors 1 and 2 is displaceable radially as shown by arrow 13 contained in the plane 11 and intersecting the axis 4.

The assembly 3 is therefore preferably displaceable radially relative to the cover 12. In which case the bed 6 includes lift means 14 for placing its top surface 5 at an appropriate height, together with a translation motor for placing the portion of the patient to be investigated level with the pair of detectors 1 and 2. These translation movements take place along arrows 15 in a direction referred to as the length direction of the detection fields 7 and 8 of the detectors 1 and 2 respectively. This is the preferred solution. However, the invention produces exactly the same results if the bed 6 is provided with means for displacing its top surface horizontally in a direction 16 perpendicular to the translation direction 15 and to the lift direction 14. It can be shown that displacements along arrows 16 in combination with displacements along arrow 14 are equivalent to displacing the set 3 of detectors radially along arrow 13. The preferred solution is described below, but it should not be forgotten that the other solution is also possible. FIG. 1 also shows a swivel-mounted display console 17 having a handle 18 enabling an operator to observe, inter alia, various machine settings.

FIG. 2 shows the means for displacing the set of two detectors 1 and 2 relative to a patient to be examined in a direction 13 which extends radially relative to the axis of rotation 4. This figure shows the set 3 of detectors 1 and 2. It also shows the outline of the cover 12. The cover 12 is fixed to a pedestal 19. Also supported by the pedestal 19 is a cylinder 20 of thickness e and coaxial with the cover. This cylinder is held behind the figure by the back of the cover 12 and it projects towards the observer perpendicularly to the plane of the FIG. 2. Near its front end, this cylinder has a circular groove 21, or optionally a projecting rib. This rib or groove 21 guides a certain number of running wheels such as 23 to 31 whose axles are held by the plane ring 32. The plane of the plane ring is perpendicular to the axis of the cylinder 20–21. The plane of the ring 32 lies in the plane of FIG. 2. The wheels retain the ring 32.

A toothed groove 33 at the periphery of the ring 32 receives a drive chain 34 driven by a motor 35. The chain 34 runs round the ring 32, passes over two driving sprockets 36 and 37, and engages a control sprocket 38. The driving sprockets are driven by the motor 35. The two driving sprockets 36 and 37 are mounted on a plate 39 which may be moved away from or towards a stand 40 which supports the sprocket 38. Thus by acting on actuators such as 41 and 42 it is possible to ensure that the chain 34 is properly tensioned in the groove 33 on the ring 32. When the motor 35 is caused to rotate, the ring 32 is thus driven around the axis 4.

The ring 32 carries another motor 43 whose driving gear wheel 44 rotates a gear wheel 45 whose axis is fixed substantially perpendicularly relative to the plane of the ring 32 (and is thus parallel to the axis 4). The motor 43 is the motor that is used for moving the pair 3 of detectors 1 and 2 away from the axis 4. To this end, the pair 3 of detectors is fixed to a T-shaped bar 46. The two flanges of the T-shaped bar 46 are fixed to the edges of the pair 3, e.g. by bolts 47 to 50. The web 51 of the T-shape of the bar 46 lying in a plane perpendicular to the plane of the figure is provided on either side with respective racks 52 and 53. These racks mesh with respective gear wheels 54 and 55 themselves driven by the gear wheel 45 via a return pulley 56 and a belt 57. The belt 57 also passes between two studs 58 and 59 mounted eccentrically on a circular plate 60 for tensioning the belt 57. When the circular plate 60 is rotated, the two studs 58 and 59 deform the path followed by the belt 56 and change its tension.

When the motor 43 rotates, the T-shaped bar 46 moves up or down in the direction of arrow 13 relative to the axis 4. The pair 3 of detectors 1 and 2 is thus easily moved closer to a patient.

One of the problems to be solved with a mechanism of this kind is obtaining a corresponding displacement of a counter weight system 61 and 62. Since the set of two detectors is relatively heavy, about 140 kg, it is important to balance it so that the tension exerted on the chain 34 is not excessive.

FIG. 3 shows a detail of the mechanism enabling the set 3 of detectors 1 and 2 to be moved synchronously with the system 61–62 of counterweights. FIG. 3 is a diagram showing the ring 32, the top of the counterweight 61, and the edge 63 of the pair 3 of detectors. The counterweights 61 and 62 are inside the cover 12, while the detectors 1 and 2 are outside it. When the set 3 moves down in the direction of arrow 64, the counterweights move symmetrically in the direction of arrow 65. A device like that shown in FIG. 3 is to be found at opposite ends of a diameter of the ring 32. Thus, there is a guide 66 fixed on each side of the pair 3 of detectors and a guide 67 fixed to the corresponding counterweight 61 (or 62). These guides are members of a generally channel-section shape. Each possesses a rack at the end of and perpendicular to one of the flanges of its channel-section shape, such as the racks 68 and 69, respectively. Toothed shafts such as 70 and 71 engage in these racks. In practice, there are three toothed shafts in each mechanism. These toothed shafts pass through holes such as 72 formed in the ring 32. When the ring is stationary, and when the set 3 of detectors is displaced using the motor 43, the guide 66 is subjected to vertical motion of the same size. In this case, the rack 68 meshing with the shafts 70 and 71 causes them to rotate. These shafts cannot move down since they are held via respective ball bearings (not shown) inside the holes 72.

By reaction, these shafts move the guide 67 symmetrically by engaging with the rack 69. The ends of the shafts 70 or 71 are fitted with guide wheels such as 73 and 74 which are held in the guides 66 and 67 respectively, firstly by engaging rods such as 75 and secondly by being held against the rack 69 (or 68 as the case may be). By having three shafts such as 70 and by holding the two counterweights 61 and 62 together at their ends, it is possible to provide the overall assembly with good rigidity. However, as can be seen in FIG. 2, to stabilise motion better, the ends of the counterweights 61 and 62 may be provided with gear wheels meshing with two racks that are likewise caused to engage a T-section bar whose web extends perpendicularly to the ring 32.

The motor 35 is the only motor that rotates the assembly, and similarly the motor 43 is the only motor that can be used to displace the detectors and to balance loads. The solution is therefore simple. In practice, the pair of detectors 1 and 2 is situated on one side of the ring 32 while the set of gear wheels linked to the motor 43 is situated inside the cover 12. Nevertheless, other similar mechanical solutions could be devised, the essential point being that the detectors are displaced radially.

FIGS. 5a to 5c give an idea of the diameter of the part that can be reconstructed depending on whether the patient is fat or thin, respectively. In each of the figures the point of intersection of the axis 4 is shown, with the axis being in alignment with the middle of the patient's body. In FIG. 5a, the patient is fat, the detectors therefore need to be moved away, and the edges 81 and 82 respectively of the fields of the detectors 1 and 2 define the circle of full reconstruction. In one example, this circle is shown as having a diameter of 150 mm. The same items in FIGS. 5b and 5c enable the diameters of the reconstructed space to increase with decreasing patient size. In the invention, in order to be able to apply the reconstruction algorithms to these diameters to be reconstructed, it is necessary to know both the effective width 83 of the field of view FOV and the position of the normal, e.g. 84 at effective width 83. In the invention, the position of the normal 84 and the effective width 83 are determined by measuring the displacement of the pair 3 of detectors 1 and 2 relative to a standard position.

FIG. 4 shows how the means implemented for achieving the object of the invention are organised. Each detector, e.g. the detector 1, is provided at its inlet face 7 with a collimator 85 lying over a scintillator 86. The scintillations produced by the scintillator 86 excite the dinodes of an array 87 of photomultiplier tubes. The currents delivered by these photomultiplier tubes are applied to a resistance matrix 88 which delivers a set of locating pulses to a counter unit 89. The counter unit is also under the control of an arithmetic and logic unit 90 via a bus 91. The projection images are stored in an image memory 92 which may contain as many pages as there are different projections acquired.

During image processing, in order to generate one or more tomographs, a program memory 93 delivers instructions that are performed by the arithmetic and logic unit 90 on the image signals contained in the image memory 92. The program memory normally includes a set of parameters contained in a parameter memory 94. In particular, this parameter memory is shown as containing the width of the field of view and the position of the centre of rotation.

Normally, in state of the art apparatus, the centre of rotation corresponds to the intersection of the normals to the centres of the detection fields 7 and 8 of the detectors 1 and 2. However, in the invention and because of the displacements, the position of the centre of rotation must be modified by an offset δ whose value is a function of the value d of the displacement of the pair 3 of detectors 1 and 2. In the example where the detectors 1 and 2 point at substantially 90° to each other, the relationship between δ and d is of the type δ=d√.2/2+constant. A similar trigonometrical relationship can be determined if the angle of inclination between the two detectors is other than 90°. However, instead of performing such calculations, a conversion table may be provided in the parameter memory enabling each value 95 of the distance d to be associated with a value 96 for the position of the centre of the effective field of view 99 and with a value 97 representing the width of the effective field of view 99. These values 96 and 97 are then entered into the program contained in the program memory 93 so that the algorithm performed by the arithmetic and logic unit 90 remains the same.

The pair 3 can be moved along the arrow 13 by means of a keyboard 98 or by some other control member such as a mouse or a track ball. Under such circumstances, the motor 43 may also be controlled by the microprocessor contained in the arithmetic and logic unit 90. In one example, a potentiometer 100 may be engaged with any one of the gears linked to the motor 43. It is electrically connected firstly to a bias voltage and secondly to ground, with its cursor giving a voltage proportional to the displacement that is actually performed. This voltage can be used firstly to servo-control the position that is to be reached and secondly it can be used to evaluate the distance d. Alternatively, the motor 43 may be a stepper type motor and measurement by means of a potentiometer 100 can be eliminated merely by counting the number of steps applied to the motor 43. The value of d is used in tables 95–97.

By acting in this way, it is shown that the invention is easily implemented since there is no need to change the processing program that such machines already possess, while the mechanical simplification is manifest since there is only one displacement to move both heads simultaneously.

In an improvement, the pair 3 of detectors may be caused to describe an elliptical path. In which case, each angular position α of the ring 32 can be associated in advance with a distance d. This can be done in the same way as in the correspondence tables 95–96 or 95–97. The distance d is then a function of angle α.

In the variant where the detectors are secured immobile on the ring 32 and where the bed only is fitted with means for displacement following the arrow 13, these displacements must be carried out as a function of the position in rotation of the ring 32. In this case, the angle α of the ring 32 is measured, for example using means similar to those required for measuring the rotation of the gear wheels linked to motor 43. The angle α thus measured is then converted, using tables of the same type as tables 95–96 or 95–97, into bed displacement instructions for following arrows 14 or 16. It can easily be seen that the movement following 13 is broken down by trigonometrical functions of the first order (sinus or cosinus) into combined movements following 14 and 16. For a given distance d, determined for instance by instructions using the keyboard 98, displacements following 14 will be for example of the d sin α type, while those following 16 will be of the d cos α type.

The starting procedure is for example as follows. For α=0 (corresponding to the vertical detector 1 as in FIG. 1, for example), the bed is displaced following arrow 13 in response to instructions given by the keyboard 98 and according to a size of the patient. When the desired position of this bed is obtained, d is validated. The value of d is set during this validating operation, since it corresponds to a preferred nearing of the axis of the patient in the bisector plane of detectors 1 and 2. The value of d is known since it corresponds to imposed and measurable movements of the bed following 14 and 16, in relation to a central stopping position. During the following tomographic acquisition, and for each value of α, the motors of the bed are caused to displace the bed according to the functions indicated above. The axis of the patient thus describes a circular movement which is concentric to the ring 12.

In a variant, the cover 12 and the ring 32 are not completely circular but form a C-shape leaving a gap through which a an examination bed can be moved closer laterally.

What is claimed is:

1. Apparatus for acquiring tomographs of a subject, the apparatus comprising a pair of plane scintillation detectors (1, 2) carried by a support (32) rotatable about an axis of rotation (4), and connected to an image processor (90–94), the apparatus being characterised in that:
    the two detectors are secured to each other,
    the detection fields (7, 8) of these two detectors are inclined at an angle relative to each other;
    the bisector plane (11) bisecting the angle formed between these detection fields includes the axis of rotation;
    and in that the apparatus includes:
        means (35–42) for displacing the pair of detectors together relative to the subject in a direction (13) which is radial to the axis of rotation; and
        modification means (94) for modifying an effective detection field (98) of these detectors as a function of said displacement.

2. Apparatus according to claim 1, characterised in that the modification means comprise:
    an arithmetic and logic unit (90) connected to:
    a sensor (100) for supplying data relating to displacement of the detectors;
    a program memory (93) containing a program for computing tomographic images; and
    a parameter memory (94) for modifying a parameter of the image-computing program as a function of the displacement.

3. Apparatus according to claim 2, characterised in the modification means comprise, connected to the arithmetic and logic unit:
    a rotation sensor for measuring rotation of the support; and
    a memory containing a path modification program for modifying the displacement of the detectors as a function of the rotary position of the support.

4. Apparatus according to any one of claims 1 to 3, characterised in that the angle of inclination formed between the detection fields is substantially equal to 90°.

5. Apparatus according to claim 1, characterized in that the edges of the detection fields of the two detectors are spaced apart by less than 2 centimeters.

6. Apparatus according to claim 1, characterized in that the apparatus includes means (65–66) for displacing detector-balancing counterweights in the opposite direction to detector displacement.

7. Apparatus according to claim 1 characterized in that the support includes a cylindrical ring (32) rotatable relative to another ring (30).

8. Apparatus according to claim 1 characterized in that the support includes a first cylindrical ring portion rotatable relative to a second cylindrical ring portion.

9. Apparatus according to claim 1, characterized in that the means for displacing the pair of detectors include a motor for displacing the pair of detectors relative to their rotary support.

10. Apparatus according to claim 1, characterized in that the means for displacing the pair of detectors comprises a motor for displacing a subject-carrying bed relative to the pair of detectors.

11. Apparatus according to claim 1, characterized in that the two detectors are fixed relative to each other by construction.

12. A method for performing a 180° SPECT scan to form a SPECT image of an organ, the organ being in the body of a patient oriented lengthwise along a lateral axis, with the organ emitting gamma radiation, said method comprising the steps of:
    providing only a pair of gamma ray detectors, each having a planar collimator surface for receiving incident gamma rays, with said detectors oriented so that the planar collimator surfaces are substantially perpendicular to a plane that is perpendicular to the lateral axis; and
    rotating said oriented detectors along a path to acquire image data at a plurality of positions along the path.

13. A method for performing a scan to form an image of an organ in the body of a patient, with the organ emitting gamma radiation, said method comprising the steps of:
    providing only a pair of gamma ray detectors, each having a planar detector surface for receiving incident gamma rays, with said detectors oriented so that the planar detector surfaces are substantially perpendicular to each other and so that the normal to each planar detector surface is substantially perpendicular to an axis of rotation used in the scan; and
    rotating said oriented detectors to acquire image data at a plurality of positions around the patient.

* * * * *